United States Patent
van der Kouwe et al.

(10) Patent No.: US 9,213,074 B2
(45) Date of Patent: Dec. 15, 2015

(54) STEM AND METHOD FOR ACQUIRING MRI DATA FROM BONE AND SOFT TISSUES

(75) Inventors: Andre van der Kouwe, Woburn, MA (US); Thomas Benner, Cambridge, MA (US)

(73) Assignee: The General Hospital Corporation, Boston, MA (US)

(*) Notice: Subject to any disclaimer, the term of this patent is extended or adjusted under 35 U.S.C. 154(b) by 1627 days.

(21) Appl. No.: 12/423,303

(22) Filed: Apr. 14, 2009

(65) Prior Publication Data
US 2010/0261993 A1 Oct. 14, 2010

(51) Int. Cl.
| | |
|---|---|
| A61B 5/05 | (2006.01) |
| G01R 33/48 | (2006.01) |
| A61B 5/055 | (2006.01) |
| G01R 33/561 | (2006.01) |

(52) U.S. Cl.
CPC .............. *G01R 33/482* (2013.01); *A61B 5/055* (2013.01); *G01R 33/4816* (2013.01); *G01R 33/4824* (2013.01); *G01R 33/5613* (2013.01); *G01R 33/481* (2013.01)

(58) Field of Classification Search
USPC .......... 600/407–410; 382/173–180, 280–278
See application file for complete search history.

(56) References Cited

U.S. PATENT DOCUMENTS

| | | | | |
|---|---|---|---|---|
| 7,465,927 B2* | 12/2008 | Panin et al. | ............... | 250/363.03 |
| 2007/0206880 A1* | 9/2007 | Chen et al. | ................... | 382/294 |
| 2009/0112081 A1* | 4/2009 | Yu et al. | ........................ | 600/410 |
| 2010/0202687 A1* | 8/2010 | Melbourne et al. | ........... | 382/173 |

OTHER PUBLICATIONS

Magnetic Resonance in Medicine, vol. 55, Issue 5, pp. 1075-1082, May 2006, Three-dimensional radial ultrashort echo-time imaging with T2 adapted sampling.*
Deoni, et al., Rapid Combined T1 and T2 Mapping Using Gradient Recalled Acquisition in the Steady State, Magnetic Resonance in Medicine, 2003, 49:515-526.
Fischl, et al., Sequence-Independent Segmentation of Magnetic Resonance Images, NeuroImage, 2004, 23:S69-S84.
Tyler, et al., Magnetic Resonance Imaging With Ultrashort TE (UTE) PULSE Sequences: Technical Considerations, Journal of Magnetic Resonance Imaging, 2007, 25:279-289.
Yu, et al., Multiecho Reconstruction for Simultaneous Water-Fat Decomposition and T2* Estimation, Journal of Magnetic Resonance Imaging, 2007, 26:1153-1161.

* cited by examiner

*Primary Examiner* — Amanda Lauritzen Moher
*Assistant Examiner* — Shahdeep Mohammed
(74) *Attorney, Agent, or Firm* — Quarles & Brady, LLP

(57) ABSTRACT

A system and method for producing MR images in which bone and soft tissue are identified. The method includes applying a pulse sequence that includes a first stage configured to acquire a radially-encoded FID and radially-encoded echoes performed after a non-selective RF excitation pulse and before a second stage, which is configured to acquire additional echoes. The radially-encoded MR data acquired during the first stage is substantially representative of bone, while the MR data acquired during the second stage is substantially representative of soft tissues. MR images in which bone and soft tissue are identified are reconstructed from these MR data sets.

10 Claims, 3 Drawing Sheets

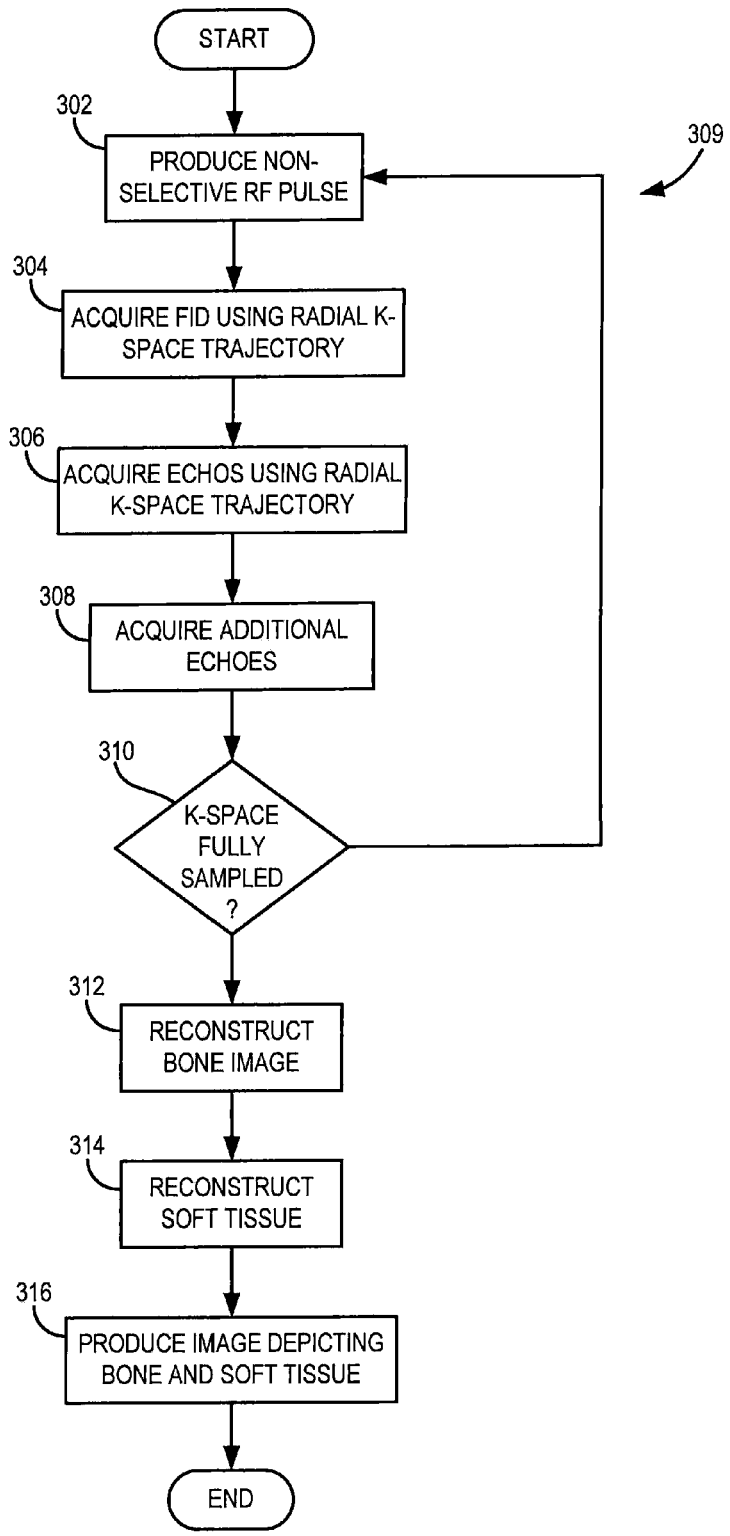

STEM AND METHOD FOR ACQUIRING MRI DATA FROM BONE AND SOFT TISSUES

BACKGROUND OF THE INVENTION

The field of the invention is magnetic resonance imaging ("MRI") methods and systems. More particularly, the invention relates to acquiring MRI data from which both bone and soft tissues can be imaged.

There are many clinical applications where it is desirable to produce medical images that enable bone and other tissues to be visualized and segmented. For example, whole head segmentation methods that include bone provide a basis for calculating attenuation and scatter correction maps for positron emission tomography (PET) imaging. The attenuation correction and scatter (AC) correction map is important for accurate PET image reconstruction and the location of dense tissues such as bone is most important. Accurate AC maps should not only include the skull but should also the other bones in the head that may scatter or attenuate the gamma photons. AC maps are usually derived from a computed tomography (CT) or PET data, but these imaging modalities have drawbacks, for example, CT imaging exposes the patient to ionizing radiation. Thus, it would be desirable to utilize an alternative imaging modality that does not require the use of ionizing radiation or administration of a radiotracer.

For example, accurate, detailed, and subject-specific head models that include muscle, bone, marrow, skin, and facial features can also allow for more accurate localization of brain activation as measured by EEG and MEG. Experimental data from healthy brains and from artificially induced dipoles in epileptic patients suggest inherent localization differences for electric potential versus magnetic field data. In these studies, however, it is difficult to separate the effect of errors in the forward solution from localization errors due to differences between EEG and MEG. Specifically, there are fundamental differences between the forward solution accuracy required by EEG and MEG, with MEG requiring a simpler model. Given sufficiently accurate forward models for both EEG and MEG, explicitly combining EEG and MEG provides more accurate activity estimates than either measure by itself. The construction of accurate and detailed head models is required to combine the data.

In optical imaging, detailed head models can allow activation patterns to be inferred from measured signals with improved accuracy. Due to the diffuse nature of the near-infrared photons that are used to sample the tissue, the spatial resolution of diffuse optical imaging is limited to roughly 1-2 cm in the adult human cortex near the skull. This low spatial resolution results in significant errors in the quantitative characterization of hemoglobin concentrations in, for example, cortex versus skull due to partial volume effects. The complex non-linear propagation of light through tissue results in a partial volume effect that does not produce a linear average of the sampled tissues. Using magnetic resonance (MR) based segmentation labels as a structural a priori data in the optical imaging inverse problem removes the partial volume averaging, and enables the quantification of hemoglobin concentrations within each tissue type.

To acquire such data, a magnetic resonance imaging (MRI) system is utilized. When a substance such as human tissue is subjected to a uniform magnetic field (polarizing field $B_0$), the individual magnetic moments of the excited nuclei in the tissue attempt to align with this polarizing field, but precess about it in random order at their characteristic Larmor frequency. If the substance, or tissue, is subjected to a magnetic field (excitation field $B_1$) that is in the x-y plane and that is near the Larmor frequency, the net aligned moment, $M_z$, may be rotated, or "tipped", into the x-y plane to produce a net transverse magnetic moment $M_t$. A signal is emitted by the excited nuclei or "spins", after the excitation signal $B_1$ is terminated, and this signal may be received and processed to form an image.

When utilizing these "MR" signals to produce images, magnetic field gradients ($G_x$, $G_y$ and $G_z$) are employed. Typically, the region to be imaged is scanned by a sequence of measurement cycles in which these gradients vary according to the particular localization method being used. The resulting set of received MR signals are digitized and processed to reconstruct the image using one of many well known reconstruction techniques. The measurement cycle used to acquire each MR signal is performed under the direction of a pulse sequence produced by a pulse sequencer. Clinically available MRI systems store a library of such pulse sequences that can be prescribed to meet the needs of many different clinical applications. Research MRI systems include a library of clinically proven pulse sequences and they also enable the development of new pulse sequences.

Bone position can been inferred from the surrounding tissue in MR images. However, in some applications, such as PET attenuation correction, all the bone in the head must be labeled and non-skull bones (lower jaw/vertebrae) can be difficult to disambiguate from the surrounding tissue. While an expert human anatomist may be able to infer the position of bone from conventional MR images, it is much harder to train an automated system to do the same. For example, such systems have been observed to label the air in the mouth as "bone" continuous with the teeth. To simply and robustly identify bone, it is best to acquire signal from the bone itself. Also, bone marrow can provide MR signal in conventional scans that may cause improper segmentation for narrow regions of the skull with relatively more marrow. In PET attenuation correction, mistaking air for bone greatly impacts the quality of the reconstructed images and could result in missed or spurious "hot spots".

Methods are known for acquiring MR images of bone. One of these employs an ultrashort TE (UTE) pulse sequence, which is used to image substances with short $T_2$ relaxation times, including bone. However, UTE pulse sequences are not suited for imaging substances with longer $T_2$ relaxation times, such as the brain tissue. Traditional pulse sequences for imaging brain morphometry, such as MPRAGE and FLASH are also well known for distinguishing surrounding soft tissues, but they are insensitive to bone. Some have tried to utilize these two separate pulse sequences to acquire both the data from the bone and the tissue in consecutive imaging acquisitions. In multispectral morphometry, it is extremely important that all images align properly and that small details defining the edges of structures are well depicted. In such consecutive imaging acquisitions, this is particularly problematic using traditional techniques because bone images acquired using one pulse sequence may not properly register with soft tissue images acquired using a different pulse sequence. This is especially true when studying narrow structures such as the cerebral spinal fluid (CSF) outside the cortex, the skull, and the layers of fat and skin outside the skull, where it is critical that images identifying the different structures align properly It would therefore be desirable to have a system and method for gathering structural information about bone and soft tissue that does not subject the patient to undesirable doses of radiation or radiotracers, is not plagued by overly complex modeling schemes, and is not subject to errors in registering sets of data corresponding to tissue and bone.

SUMMARY OF THE INVENTION

The present invention overcomes the aforementioned drawbacks by providing a system and method for producing MR images from which both bone and soft tissue can be identified. Inaccuracies accompanying the registration of bone images and soft tissue images from different MR scans are avoided by using a pulse sequence configured to acquire both bone MR data and soft tissue MR data. Because the MR data from bone can be acquired in a short time window between the production of an RF excitation pulse and the acquisition of MR data soft tissue, no significant increase in scan time is incurred over traditional soft tissue morphometry pulse sequences.

The present invention provides a method for producing an MR image that can be automatically segmented between bone and soft tissue. The method comprises performing a pulse sequence with an MRI system that includes producing a non-selective RF pulse, acquiring an MR signal from a free-induction-decay having an ultra-short echo time using a radial k-space trajectory, acquiring at least one MR signal from at least one echo using a radial k-space trajectory, and acquiring a plurality of MR signals from additional echoes. The method further comprises repeating the pulse sequence a plurality of times to acquire a selected amount of MR signals and reconstructing an MR image depicting both bone and soft tissue. The MR image depicting bone and soft tissue is produced by reconstructing an image substantially indicative of bone from the MR signals acquired from the FID and echoes using the radial k-space trajectory, reconstructing an image substantially indicative of soft tissues from the plurality of MR signals acquired from the additional echoes, and combining these images to produce the MR image depicting both bone and soft tissue.

Various other features of the present invention will be made apparent from the following detailed description and the drawings

BRIEF DESCRIPTION OF THE DRAWINGS

FIG. 3 is a flowchart setting forth the steps of producing MR images in accordance with the present invention.

DESCRIPTION OF THE PREFERRED EMBODIMENT

Figure 1:
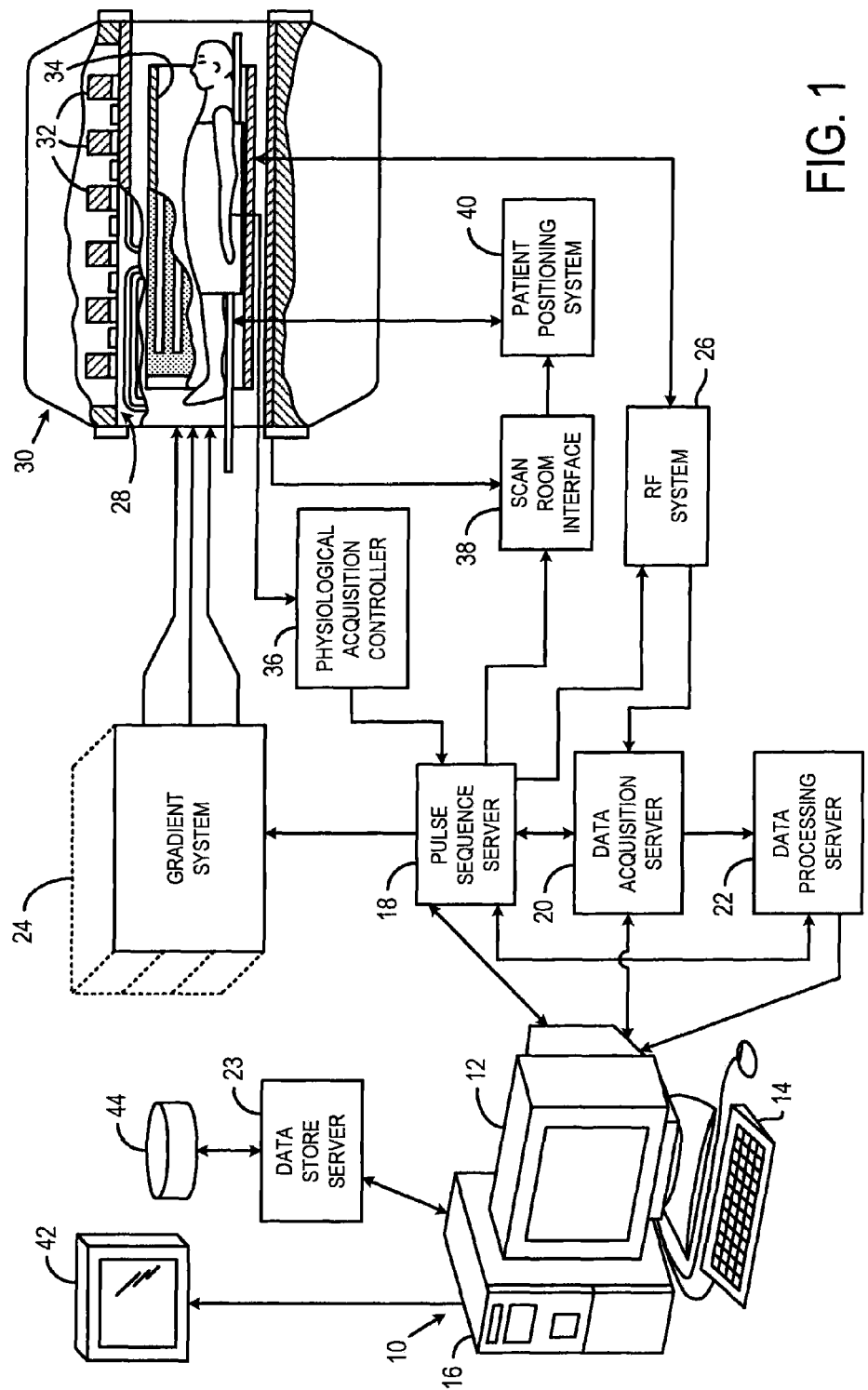
FIG. 1 is a block diagram of an MRI system that employs the present invention.

Referring particularly to FIG. 1, the preferred embodiment of the invention is employed in an MRI system. The MRI system includes a workstation 10 having a display 12 and a keyboard 14. The workstation 10 includes a processor 16 that is a commercially available programmable machine running a commercially available operating system. The workstation 10 provides the operator interface that enables scan prescriptions to be entered into the MRI system. The workstation 10 is coupled to four servers: a pulse sequence server 18; a data acquisition server 20; a data processing server 22, and a data store server 23. The workstation 10 and each server 18, 20, 22 and 23 are connected to communicate with each other.

The pulse sequence server 18 functions in response to instructions downloaded from the workstation 10 to operate a gradient system 24 and an RF system 26. Gradient waveforms necessary to perform the prescribed scan are produced and applied to the gradient system 24 that excites gradient coils in an assembly 28 to produce the magnetic field gradients $G_x$, $G_y$ and $G_z$ used for position encoding MR signals. The gradient coil assembly 28 forms part of a magnet assembly 30 that includes a polarizing magnet 32 and a whole-body RF coil 34.

RF excitation waveforms are applied to the RF coil 34 by the RF system 26 to perform the prescribed magnetic resonance pulse sequence. Responsive MR signals detected by the RF coil 34 or a separate local coil (not shown in FIG. 1) are received by the RF system 26, amplified, demodulated, filtered and digitized under direction of commands produced by the pulse sequence server 18. The RF system 26 includes an RF transmitter for producing a wide variety of RF pulses used in MR pulse sequences. The RF transmitter is responsive to the scan prescription and direction from the pulse sequence server 18 to produce RF pulses of the desired frequency, phase and pulse amplitude waveform. The generated RF pulses may be applied to the whole body RF coil 34 or to one or more local coils or coil arrays (not shown in FIG. 1).

The RF system 26 also includes one or more RF receiver channels. Each RF receiver channel includes an RF amplifier that amplifies the MR signal received by the coil to which it is connected and a detector that detects and digitizes the I and Q quadrature components of the received MR signal. The magnitude of the received MR signal may thus be determined at any sampled point by the square root of the sum of the squares of the I and Q components:

$$M=\sqrt{I^2+Q^2},$$

and the phase of the received MR signal may also be determined:

$$\phi=\tan^{-1} Q/I.$$

The pulse sequence server 18 also optionally receives patient data from a physiological acquisition controller 36. The controller 36 receives signals from a number of different sensors connected to the patient, such as ECG signals from electrodes or respiratory signals from a bellows. Such signals are typically used by the pulse sequence server 18 to synchronize, or "gate", the performance of the scan with the subject's respiration or heart beat.

The pulse sequence server 18 also connects to a scan room interface circuit 38 that receives signals from various sensors associated with the condition of the patient and the magnet system. It is also through the scan room interface circuit 38 that a patient positioning system 40 receives commands to move the patient to desired positions during the scan.

The digitized MR signal samples produced by the RF system 26 are received by the data acquisition server 20. The data acquisition server 20 operates in response to instructions downloaded from the workstation 10 to receive the real-time MR data and provide buffer storage such that no data is lost by data overrun. In some scans the data acquisition server 20 does little more than pass the acquired MR data to the data processor server 22. However, in scans that require information derived from acquired MR data to control the further performance of the scan, the data acquisition server 20 is programmed to produce such information and convey it to the pulse sequence server 18. For example, during prescans MR data is acquired and used to calibrate the pulse sequence performed by the pulse sequence server 18. Also, navigator signals may be acquired during a scan and used to adjust RF or gradient system operating parameters or to control the view order in which k-space is sampled. And, the data acquisition server 20 may be employed to process MR signals used to detect the arrival of contrast agent in an MRA scan. In all these examples the data acquisition server 20 acquires MR data and processes it in real-time to produce information that is used to control the scan.

The data processing server 22 receives MR data from the data acquisition server 20 and processes it in accordance with instructions downloaded from the workstation 10. Such processing may include, for example: Fourier transformation of raw k-space MR data to produce two or three-dimensional images; the application of filters to a reconstructed image; the performance of a backprojection image reconstruction of acquired MR data; the calculation of functional MR images; the calculation of motion or flow images, etc.

Images reconstructed by the data processing server 22 are conveyed back to the workstation 10 where they are stored. Real-time images are stored in a data base memory cache (not shown) from which they may be output to operator display 12 or a display that is located near the magnet assembly 30 for use by attending physicians. Batch mode images or selected real time images are stored in a host database on disc storage 44. When such images have been reconstructed and transferred to storage, the data processing server 22 notifies the data store server 23 on the workstation 10. The workstation 10 may be used by an operator to archive the images, produce films, or send the images via a network to other facilities.

Figure 2:
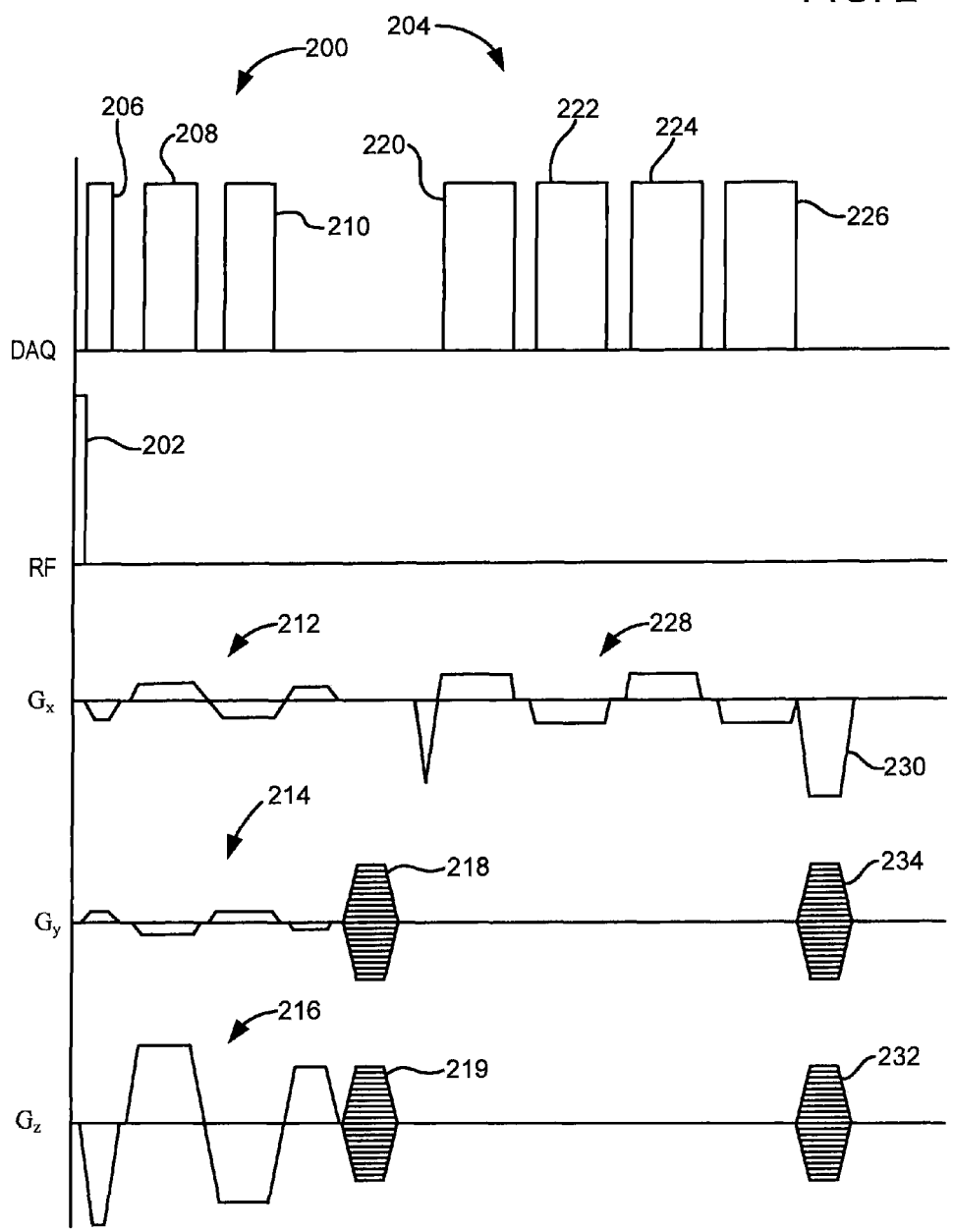
FIG. 2 is a graphic representation of a pulse sequence in accordance with the present invention that can be employed to acquire MR data with the MRI system of FIG. 1 to image both bone and tissue.

Referring to FIG. 2, a pulse sequence for acquiring MR data using the MRI system of FIG. 1 in accordance with the present invention is shown. Generally, the pulse sequence includes a first stage 200 for acquiring radially-encoded NMR signals substantially representative of bone performed after an RF excitation pulse 202 and before a second stage 204 for acquiring NMR signals substantially representative of soft tissue. While a variety of configurations can be used, it is contemplated that the first stage 200 is an ultra-short echo time (UTE) sequence and the second stage 204 is a fast low angle shot (FLASH) sequence, as is depicted in FIG. 2. In this particular pulse sequence, three radial projection views are acquired in the first stage during three data acquisition windows 206, 208, and 210 while applying the $G_x$, $G_y$, and $G_z$ readout gradients, 212, 214, and 216, respectively. The first acquired MR signal is a free-induction-decay signal (FID) and the following two signals are gradient recalled echo (GRE) signals with short echo times (TE). A radial k-space sampling trajectory is provided by progressively changing the readout gradients $G_x$, $G_y$, and $G_z$, 212, 214, and 216, respectively, during a scan to uniformly sample a three-dimensional volume about the center of k-space. Thus, the FID and echoes of the first stage 200 may be referred to as "radially-encoded." Different implementations of the pulse sequence may acquire different numbers of radially-encoded echoes at different TEs depending on scan-specific requirements, though it is contemplated that the FID should have a minimum TE of 70 µs. In the depicted pulse sequence, which includes an RF pulse having a 20 degree flip angle and is performed at 2298 Hz/px with a 2 mm$^3$ resolution, the FID is acquired at TE=0.07 ms and the two radially-encoded echoes are acquired at 1.52 ms and 2.85 ms. In an alternate pulse sequence, the FID may be acquired at TE=0.07 ms and a single echo may be acquired at TE=2.4 ms.

In the depicted pulse sequence, additional MR data corresponding to longer TEs is acquired from the same three-dimensional volume during the second stage 204 using a FLASH-based Cartesian k-space sampling trajectory. Specifically, a $G_y$ phase encoding pulse 218 and a $G_z$ phase encoding gradient pulse 219 are applied and four echoes are acquired at data acquisition windows 220, 222, 224, and 226 in the presence of an alternating $G_x$ readout gradient 228. The pulse sequence concludes with a spoiler gradient pulse 230 along the read axis and rephasing pulses 232 and 234 along the slice select and phase encoding axes. Again, the number of echoes acquired during the second stage 204 can vary depending on scan-specific requirements. In the depicted pulse sequence, the echoes have TE=6.74, 8.33, 9.92 and 11.51 ms and are acquired at 840 Hz/px and at a resolution of 1.3×1.3×2.0 mm$^3$. As a result, the TR of the entire pulse sequence is 15 ms and a scan typically requires 4 minutes and 36 seconds to complete.

Because the first pulse sequence stage 200 occurs within a very small time window immediately after the non-selective excitation pulse 202, its presence has no significant effect the echo times of the second stage or overall TR. Therefore, inclusion of the first stage allows MR data for bone to be acquired before the acquisition of MR data for soft tissues without extending the duration of the data acquisition. In contrast to traditional brain morphometry sequences, which are insensitive to bone, the present invention allows bone to be imaged directly and registered with morphometry images. This is especially advantageous for bones other than the skull whose structures can be difficult to infer from surrounding tissue.

Referring now to FIG. 3, a method for producing an MR image depicting both bone and soft tissue begins at process block 302 with the production of a non-selective RF pulse to excite spins in a subject being imaged. At process block 304 the radially-encoded FID having an ultra-short TE is acquired and, shortly thereafter, at least one radially-encoded echo is acquired at process block 306. This radially-encoded MR data is substantially representative of short $T_2^*$ species, such as bone. Following the radial acquisition, additional echoes corresponding to longer TEs are acquired at process block 308. For example, the above FLASH-based sequence may be employed to acquire Cartesian-encoded echoes. As indicated by the loop 309, this acquisition process continues until, at decision block 310, it is determined that k-space is fully sampled. This cycle may include progressively changing the readout gradients to radially sample a three-dimensional volume about the center of k-space and stepping through a series of phase and slice encodes if employing a Cartesian k-space sampling trajectory for the second stage. The number of encoding steps can be chosen to be the same for both the first and second acquisition stages while still adequate resolution for each.

Following the acquisition of MR data, an image substantially indicative of short $T_2^*$ structures such as bone is reconstructed at process block 312 from the radially-encoded FID and echo data acquired at process blocks 304 and 306. The bone image may echo from an image reconstructed from the radially-encoded FID. However, this particular approach does not always result in sufficiently pure bone images, because, at lower resolutions, image voxels representing thin structures like skull overlap adjacent tissue containing fat and water. Therefore, to better disambiguate water and fat, images substantially indicative of bone may be produced by fitting exponentials to images reconstructed from the radially-encoded data. This may be achieved using the following model:

$$s(T_E) = (we^{-R^*_{2w}T_E} + fe^{(-R^*_{2f}T_E + i2\pi\Delta f \cdot T_E)})e^{i(\psi T_E + \phi)} \qquad \text{Eqn. 1;}$$

where $s(T_E)$ denotes MR data at a given echo time $T_E$, $\omega$ and f are water and fat fractions, respectively, $\Delta f$ is the fat-water shift, $R^*_2$ is the relaxation rate, $\psi$ is the $B_0$ magnetic field offset, and $\phi$ is a fixed phase offset in the measurement due to phase shifts in the amplifier and other errors. Water and fat may then be segmented by thresholding the signals output by the model. Bone may be identified as tissue for which the model output signals for the first radially-encoded echo fall within a selected range while model output signals for successive radially-encoded echoes fall below a selected threshold.

At process block 314, an image substantially indicative of soft tissue is reconstructed from the additional echo signals acquired at process block 308. For example, this may be achieved using the T2*-IDEAL algorithm, which uses an iterative method to estimate a complex field map incorporating $R^*_2$ and magnetic field inhomogenieties. At process block 316, an image depicting both bone and soft tissue is produced by combining the bone images produced at process block 312 with the soft tissue images produced at process block 314. In this way, information from all of the acquired NMR signals is utilized to provide improved tissue segmentation. For example, bone may be limited to image areas where soft tissue is not identified.

Such an image that is automatically and accurately segmented for tissue and bone may be used, for example, in applications ranging from EEG and MEG inverse modeling to PET attenuation correction and radiation therapy dose calibration. Further, by collecting test data with redundant echoes and analyzing subsets of the echoes, the number of radially-encoded echoes necessary to reliably fit short $T_2$ components such as bone can be determined. Thus, a quantitative basis for recommending protocols for bone imaging depending on applications is provided. For example, the above-discussed, two echo subtraction technique for producing an image indicative of bone may be acceptable when resolution and accuracy are not critical.

The present invention has been described in terms of the preferred embodiment, and it should be appreciated that many equivalents, alternatives, variations, and modifications, aside from those expressly stated, are possible and within the scope of the invention. Therefore, the invention should not be limited to a particular described embodiment

The invention claimed is:

1. A method for producing a magnetic resonance (MR) image that depicts both bone and soft tissue, the steps of the method comprising:
 a) directing a magnetic resonance imaging (MRI) system to perform a pulse sequence a plurality of times, wherein each repetition of the pulse sequence includes:
  a) i) producing a non-selective radio frequency (RF) pulse;
  a) ii) acquiring during a first stage of the pulse sequence:
   an MR signal from a free-induction-decay having an ultra-short echo time using a radial k-space trajectory; and
   at least one MR signal from at least one echo occurring after the free-induction decay using a radial k-space trajectory; and
  a) iii) acquiring during a second stage of the pulse sequence that occurs after the first stage of the pulse sequence, a plurality of MR signals from echoes occurring after the at least one echo occurring in step a) ii); and
 b) producing an MR image that depicts both bone and soft tissue by:
  b) i) reconstructing an image that depicts substantially only bone from the MR signals acquired in the first stage of the pulse sequence;
  b) ii) reconstructing an image that depicts soft tissues from the plurality of MR signals acquired in second stage of the pulse sequence; and
  b) iii) combining the images reconstructed in steps b) i) and b) ii) to produce the MR image depicting both bone and soft tissue.

2. The method as recited in claim 1 wherein the plurality of MR signals acquired in the second stage of the pulse sequence are acquired using a Cartesian k-space trajectory.

3. The method as recited in claim 1 wherein step b) i) includes:
 reconstructing a first image from the MR signals acquired from the free-induction decay in the first stage of the pulse sequence;
 reconstructing a second image from the at least one MR signal acquired from the at least one echo in the first stage of the pulse sequence; and
 combining the first image with the second image.

4. The method as recited in claim 3 wherein combining the first image with the second image includes determining a difference between the first image and the second image.

5. The method as recited in claim 3 wherein combining the first image with the second image includes employing a non-linear least squares technique to fit exponentials to the first image and the second image.

6. The method as recited in claim 3 wherein combining the first image with the second image includes employing a model to fit multiple exponentials to magnitude and phase data in the first image and the second image.

7. The method as recited in claim 6 wherein the models use the relationship:

$$s(T_E) = (we^{-R^*_{2w} T_E} + fe^{(-R^*_{2f} + i2\pi\Delta f) \cdot T_E}) e^{i(\psi T_E + \phi)}$$

in which $s(T_E)$ denotes MR signals at a given echo time, $T_E$; w is a water fraction; $R_2^*$ is a relaxation rate; f is a fat fraction; $\Delta f$ is a fat-water shift value; $\psi$ is magnetic field offset; and $\phi$ is a phase offset.

8. The method as recited in claim 1 wherein step b)iii) includes restricting bone to locations where soft tissue is not identified.

9. The method as recited in claim 1 further comprising employing the MR image depicting bone and soft tissue reconstructed in step b) as a priori information in a selected application.

10. The method as recited in claim 9 wherein the selected application is at least one of generating attenuation and scatter correction maps for positron emission tomography, calculating forward models in electroencephalography and magnetoencephalography, and solving inverse problems in optical imaging.

* * * * *

UNITED STATES PATENT AND TRADEMARK OFFICE
CERTIFICATE OF CORRECTION

| | | |
|---|---|---|
| PATENT NO. | : 9,213,074 B2 | |
| APPLICATION NO. | : 12/423303 | |
| DATED | : December 15, 2015 | |
| INVENTOR(S) | : Andre van der Kouwe et al. | |

It is certified that error appears in the above-identified patent and that said Letters Patent is hereby corrected as shown below:

Title Page, Item (54) and in the Specification, Column 1, line 1, in the title, "STEM" should be --SYSTEM--.

Claims

Claim 1, column 8, line 7, "in second" should be --in the second--.

Signed and Sealed this
Fifteenth Day of March, 2016

Michelle K. Lee
*Director of the United States Patent and Trademark Office*